US009550959B2

(12) United States Patent
Schaper et al.

(10) Patent No.: US 9,550,959 B2
(45) Date of Patent: Jan. 24, 2017

(54) PERFUME COMPOSITION

(71) Applicant: Symrise AG, Holzminden (DE)

(72) Inventors: Sabine Schaper, Holzminden (DE); Mathias Werner, Holzminden (DE); Marcus Eh, Holzminden (DE); Pierre Kurzenne, Bois-Colombes (FR)

(73) Assignee: Symrise AG, Holzminden (DE)

( * ) Notice: Subject to any disclaimer, the term of this patent is extended or adjusted under 35 U.S.C. 154(b) by 119 days.

(21) Appl. No.: 13/887,903

(22) Filed: May 6, 2013

(65) Prior Publication Data

US 2014/0147404 A1   May 29, 2014

(30) Foreign Application Priority Data

May 7, 2012  (EP) .................... 12 167037

(51) Int. Cl.
| | |
|---|---|
| *C11B 9/00* | (2006.01) |
| *A61Q 13/00* | (2006.01) |
| *A61Q 15/00* | (2006.01) |
| *C11D 3/18* | (2006.01) |
| *C11D 3/20* | (2006.01) |
| *C11D 3/50* | (2006.01) |
| *C11D 3/00* | (2006.01) |
| *A61K 8/365* | (2006.01) |
| *A61K 8/92* | (2006.01) |

(52) U.S. Cl.
CPC ............. *C11B 9/0019* (2013.01); *A61K 8/365* (2013.01); *A61K 8/922* (2013.01); *A61Q 13/00* (2013.01); *A61Q 15/00* (2013.01); *C11B 9/0003* (2013.01); *C11B 9/0034* (2013.01); *C11D 3/0068* (2013.01); *C11D 3/188* (2013.01); *C11D 3/2093* (2013.01); *C11D 3/50* (2013.01)

(58) Field of Classification Search
CPC ........ A61K 8/365; A61Q 13/00; A61Q 15/00; C11D 3/0068; C11D 3/188; C11D 3/2093; C11D 3/50
See application file for complete search history.

(56) References Cited

U.S. PATENT DOCUMENTS

| | | | | |
|---|---|---|---|---|
| 4,299,737 | A | * | 11/1981 | Meffert et al. .................. 512/2 |
| 2006/0251597 | A1 | | 11/2006 | Yu et al. |
| 2009/0163733 | A1 | | 6/2009 | Joulain et al. |
| 2011/0033405 | A1 | | 2/2011 | Mobarak |

FOREIGN PATENT DOCUMENTS

| | | |
|---|---|---|
| EP | 24517 A1 | 3/1981 |
| EP | 1600151 A1 | 11/2005 |
| JP | 07126685 A * | 5/1995 |
| JP | 2009172189 A | 8/2009 |
| WO | 2008044046 A1 | 4/2008 |
| WO | WO 2009090355 A1 * | 7/2009 |

OTHER PUBLICATIONS

Aochi et al, JP 07126685 A, 1995, abstract.*
Sun (Alternative Medicine Review, 2007, vol. 12, pp. 259-264).*
Mondello et al (Journal of Essential Oil Research, 1996, vol. 8, pp. 597-609).*
Clark et al (Economic Botany, 1981, vol. 35, pp. 59-69).*
Cho et al (Journal of Applied Phycology, 2005, vol. 17, pp. 431-435).*
Upton et al (Microbiology, 2007, vol. 153, pp. 3973-3982).*

* cited by examiner

*Primary Examiner* — Mark V Stevens
(74) *Attorney, Agent, or Firm* — Dilworth & Barrese, LLP

(57) ABSTRACT

Suggested is a perfume composition, comprising
(a) Petit grain oil and
(b) Hydroxy carboxylic acid esters,
which is particular useful for fighting various malodors.

24 Claims, No Drawings

PERFUME COMPOSITION

FIELD OF INVENTION

The present invention belongs to the area of detergents and personal care products and refers to an improved perfume composition for fighting various malodours.

STATE OF THE ART

The problem of malodours has been recognised for many years, and numerous methods have been developed to overcome these where they occur. Perfumes are commonly used as malodour counteractants either alone or in combination with other materials such as absorbents, oxidants and other actives.

Perfumes generally have some capability to neutralise specific types of malodours, this effect arising in large part from the phenomenon of 'odour masking' wherein the perfume intensity is sufficiently high to swamp or distort the olfactory perception of malodour. For example 3-mercapto-3-methyl-hexan-1-ol that is very active in masking sweat odour (EP 1763373 A1, Symrise). Often, however, the dosage levels of perfume required to obtain effective masking are outside the dosage levels preferred by product formulators and liked by customers.

On the other hand, it is known that certain perfumes are surprisingly more effective against specific malodours than other, and this activity is not explainable only in terms of odour masking. For example, GB 2,016,507 A1, U.S. Pat. No. 4,134,838, U.S. Pat. No. 4,663,068, GB 2,013,493 A1, EP 0404470 A1 (all Unilever) and EP 1269983 B1 (Symrise) all describe different perfumes which offer deodorant activity against body odour when incorporated into various products (as for example soaps, fabric treatment products, skin products).

As a matter of fact, the state of the art knows a lot of perfumes which are effective against special types of malodours, but there is a constant need for perfumes which have high activity against for example smoke malodour and simultaneously against kitchen smells, bathroom smells and the like. The problem underlying the present invention addresses the needs explained above. In particular it has been the object of the present invention to provide perfume compositions that are suitable for fighting various types of malodours; in particular malodours caused by cigarette smoke and are active at low concentrations. An additional object has been to provide compositions that are easy and stable to incorporate into a variety of detergent and personal care products.

DESCRIPTION OF THE INVENTION

Object of the present invention is a perfume composition, comprising
(a) Petit grain oil and
(b) Hydroxy carboxylic acid esters.

Surprisingly, it has been observed that perfume compositions comprising the components (a) and (b), optionally together with certain terpenes and/or selected essential oils show a synergistic behaviour and are suitable to fight various malodours simultaneously. The compositions have been found particularly useful as additives for perfuming detergents and personal care compositions, such as e.g. manual washing agents, all-purpose cleaners, but also deodorants and related products which are either brought into contact with hard surfaces or human skin. It has also been found that the perfume compositions are highly active at very low levels and can be incorporated into various consumer products without causing problems to storage stability.

Petit Grain Oil

Petit grain is an essential oil (Component a) that is extracted from the green twigs of the bitter orange plant (*Citrus aurantium* var. *amara*) via steam distillation. The oil is often used for aroma therapy and provides a fresh, woody and slightly floral note. The main constituents of petit grain oil are provided in Table I:

TABLE I

| Composition of Petit grain oil (CAS 8014-17-3) | |
|---|---|
| Compound | Structure |
| Geraniol | [structure] |
| Geranyl acetate | [structure] |
| Linalool | [structure] |
| Linalyl acetate | [structure] |
| Myrcene | [structure] |
| Nerol | [structure] |

TABLE I-continued

Composition of Petit grain oil (CAS 8014-17-3)

| Compound | Structure |
|---|---|
| Neryl acetate | 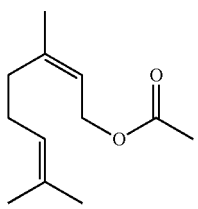 |
| Terpineol | 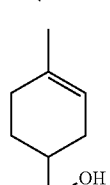 |

Hydroxy Carboxylic Acid Esters

Hydroxy carboxylic acid esters forming component (b) can be selected from $C_1$-$C_4$ alkyl esters of citric acid, malic acid and/or tartric acid. Minor preferred are esters from those hydroxylic acid esters which do not provide a specific flavour, like for example esters of lactic acid or ricinoleic acid. On the other hand, the preferred esters are methyl, ethyl, propyl and/or butyl esters of citric acid. Component (b) encompasses mono, di and triesters of these acids and of course their statistical mixtures. In particular preferred is triethyl citrate.

Terpenes

As an optional ingredient the compositions according to the present invention may comprise terpenes (component c). These compounds have been found to increase the performance of the mixtures of component (a) and (b) especially with respect to fighting cigarette smoke. Suitable terpenes encompass the following examples:

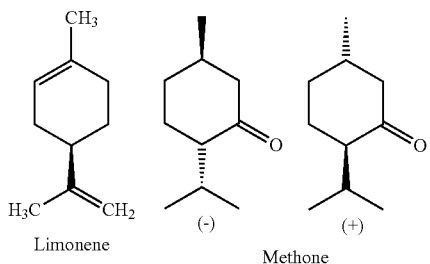

Selected Essential Oils

According to another preferred embodiment of the present invention the compositions may comprise as optional ingredients (d) essential oils selected from the group consisting of citronella oil, lavender oil, litsea cubeba oil, palmarosa oil, peppermint oil, pine oil and their mixtures.

Citronella oil (component d1) is one of the essential oils obtained from the leaves and stems of different species of *Cymbopogon* (lemongrass). The oil is used extensively as a source of perfumery chemicals such as citronellal, citronellol and geraniol. These chemicals find extensive use in soap, perfumery, cosmetic and flavouring industries throughout the world. Citronella oil is classified in trade into two chemotypes:

(a) Ceylon type (CAS: 89998-15-2; CAS: 8000-29-1; EINECS: 289-753-6; FEMA: 2308). The oil is typically obtained from *Cymbopogon nardus* Rendle and consists of geraniol (18-20%), limonene (9-11%), methyl isoeugenol (7-11%), citronellol (6-8%), and citronellal (5-15%)

(b) Java type (CAS: 91771-61-8; CAS: 8000-29-1; EINECS: 294-954-7; FEMA: 2308) The oil is typically obtained from *Cymbopogon winterianus* Jowitt and consists of citronellal (32-45%), geraniol (11-13%), geranyl acetate (3-8%), limonene (1-4%).

The higher proportions of geraniol and citronellal in the Java type make it a better source for perfumery derivatives. Both types, however, are probably originated from Mana Grass of Sri Lanka, which according to Finnemore (1962) occurs today in two wild forms—*Cymbopogon nardus* var. *linnae* (typicus) and *C. nardus* var. *confertiflorus*. Neither wild form is known to be used for distillation to any appreciable extent. Citronella oil from *Cymbopogon* species should not be confused with other similar lemony oils from *Corymbia citriodora* and *Pelargonium citrosum*.

Lavender oil (component d2) is an essential oil obtained by distillation from the flower spikes of certain species of lavender. Two forms are distinguished, lavender flower oil, a colorless oil, insoluble in water, having a density of 0.885 g/mL; and lavender spike oil, a distillate from the herb *Lavandula latifolia*, having density 0.905 g/mL. Lavender flower oil is a designation of the National Formulary and the British Pharmacopoeia. Like all essential oils, it is not a pure compound; it is a complex mixture of naturally occurring phytochemicals, including linalool and linalyl acetate. Kashmir Lavender oil is famous for being produced from lavender at the foothills of the Himalayas.

The primary components of lavender oil are linalool (51%) and linalyl acetate (35%). Other components include α-pinene, limonene, 1,8-cineole, cis- and trans-ocimene, octanone, camphor, caryophyllene, terpinen-4-ol and lavendulyl acetate. Table II provides an overview of a typical composition of two different lavender compositions.

TABLE II

Composition of lavender compositions

| Family | Composition | Lavande officinale *Lavandula angustifolia* | Lavande aspic *Lavandula latifolia* |
|---|---|---|---|
| Terpenes/Monoterpenols | 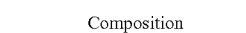 Linalool | 28.92% | 49.47% |

TABLE II-continued

Composition of lavender compositions

| Family | Composition | Lavande officinale *Lavandula angustifolia* | Lavande aspic *Lavandula latifolia* |
|---|---|---|---|
| | Alpha-terpineol | 0.90% | 1.08% |
| | Gamma-terpineol | | 0.09% |
| | Borneol | | 1.43% |
| | Iso-borneol | | 0.82% |
| | Terpinen-4-ol | 4.32% | |
| | Nerol | 0.20% | |
| | Lavandulol | 0.78% | |
| Terpenes/ Terpene esters | 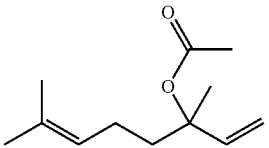 Linalyl acetate | 32.98% | |
| | Geranyl acetate | 0.60% | |
| | Neryl acetate | 0.32% | |
| | Octene-3-yl acetate | 0.65% | |
| | Lavandulyl acetate | 4.52% | |
| Terpenes/ Monoterpenes | Myrcene | 0.46% | 0.41% |
| | alpha-pinene | | 0.54% |
| | beta-pinene | | 0.33% |
| | Camphene | | 0.30% |
| | E-beta-ocimene | 3.09% | |
| | Z-beta-ocimene | 4.44% | |
| | beta-phellandrene | 0.12% | |
| Terpenes/ Terpenoid oxides | 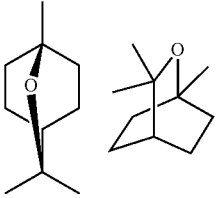 Eucalyptol (1,8-cineol) | | 25.91% |
| Terpenes/ Sesquiterpenes | beta-caryophyllene | 4.62% | 2.10% |
| | beta-farnesene | 2.73% | |
| | Germacrene | 0.27% | |
| | alpha-humulene | | 0.28% |
| Ketones | 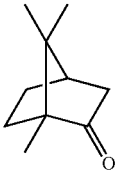 Camphor | 0.85% | 13.00% |
| | Octanone-3 | 0.72% | |
| | Cryptone | 0.35% | |

Litsea cubeba oil, also known as May Chang oil, (component d3) is an essential oil obtained from an evergreen tree or shrub 5-12 meters high in the Lauraceae family. It is native to China, Indonesia, Taiwan and other parts of Southeast Asia. It is called "mountain pepper" (山胡椒) in Mandarin and maqaw (馬告) by the Atayal aborigines in Taiwan. It produces a fruit which is processed for its lemony essential oil. The oil can also be extracted from the leaf, but this is considered to be lower in quality. The timber is sometimes used for making furniture and crafts. Plant parts are also used in medicine Palmarosa is the common name for *Cymbopogon martini*, a species of grass in the lemon grass genus. Other common names include Indian geranium and rosha or rosha grass. This perennial grass is native to Southeast Asia, especially India, and it is cultivated for its oil. The essential oil of this plant (component d4), which contains the active compound geraniol, is valued for its scent and for a number of traditional medicinal and household uses.

Peppermint (Mentha×piperita, also known as *M. balsamea* Willd.) is a hybrid mint, a cross between watermint and spearmint. The plant, indigenous to Europe, is now widespread in cultivation throughout all regions of the world. It is found wild occasionally with its parent species. Peppermint oil (component d5) has a high concentration of natural pesticides, mainly menthone.

Pine oil (component d6) is an essential oil obtained by the steam distillation of needles, twigs and cones from a variety of species of pine, particularly *Pinus sylvestris*. Chemically, pine oil consists mainly of cyclic terpene alcohols. It may also contain terpene hydrocarbons, ethers, and esters. The exact composition depends on various factors such as the variety of pine it is produced from and the parts of the tree used.

In another preferred embodiment the compositions according to the present invention may comprise terpenes and essential oils selected from the group consisting of citronella oil, lavender oil, litsea cubeba oil, palmarosa oil, peppermint oil, pine oil and their mixtures.

More particularly said compositions comprise
(a) about 0.1 to about 40% b.w., preferably about 0.5 to about 25% b.w., and most preferably about 1 to about 15% b.w. petit grain oil,
(b) about 99.9 to about 60% b.w., preferably about 90 to about 65% b.w., and most preferably about 90 to about 80% b.w. hydroxy carboxylic acid esters,
(c) 0 to about 25% b.w., preferably 1 to 20% b.w. and most preferably 5 to 15% b.w. terpenes, and
(d) 0 to about 25% b.w., preferably 1 to 20% b.w. and most preferably 5 to 15% b.w. essential oils
on condition that the amounts add to 100% b.w.

A preferred embodiment of the present invention encompasses a combination of Petitgrain and Peppermint Oil. Particularly preferred is a mixture comprising the two components in a weight ratio of about 10:1 to about 1:10. A critical feature within this embodiment is the ration by weight of the main ingredients. Therefore, a mixture comprising the components linalool:linaly lacetate:menthol:m-enthone in weight ratios of about (1-3):(2.5-5.5):(1-3.5):(0.5-2.5) has been found to be very advantageous.

Industrial Application

The present invention also encompasses various ready-to-use compositions, such as for example, but not limited to
detergent compositions, in particular hard surface cleaning compositions such as e.g. manual dish washing compositions, all-purpose cleaning compositions, but also light duty detergent compositions and the like; or personal care compositions, such as e.g. deodorant compositions, shampoos, shower gels and the like
containing a perfume composition comprising (a) Petit grain oil and (b) hydroxy carboxylic acid esters, and optionally (c) terpenes and/or (d) additional essential oils. In particular these products are liquid, pasty or represent sticks. The perfume compositions may be incorporated into the products in amounts of 0.01 to 5, preferably 0.1 to 2 and more preferably 0.5 to 1% b.w.

Another embodiment of the present invention is directed to a method for reducing malodours, as for example kitchen smells, bathroom smells, smoke and/or sweat, by applying the perfume composition of the invention to hard surfaces or human skin.

Finally, the invention also covers the use of said perfume compositions for fighting malodours such as for example kitchen smells, bathroom smells, smoke and/or sweat.

Detergent Compositions

As explained above, the perfume compositions according to the present invention are useful for perfuming various detergent compositions that are intended for cleaning hard surfaces, such as for example manual dish washing agents or all-purpose cleaners. Obviously, the invention is not limited to these two examples, also similar products as for example automatic dishwashing compositions, rinsing agents, light duty detergents or sprays for removing malodours from textiles are encompassed by the invention.

These compositions may also include various additives such as, for example, anionic, nonionic, cationic, amphoteric or zwitterionic (co-)surfactants, organic solvents, enzymes and additional auxiliaries such as soil repellents, thickeners, colorants and the like.

Anionic Surfactants

Preferably, surfactants of the sulfonate type, alk(en)yl sulfonates, alkoxylated alk(en)yl sulfates, ester sulfonates and/or soaps are used as the anionic surfactants. Suitable surfactants of the sulfonate type are advantageously $C_{9-13}$ alkylbenzene sulfonates, olefin sulfonates, i.e. mixtures of alkene- and hydroxyalkane sulfonates, and disulfonates, as are obtained, for example, by the sulfonation with gaseous sulfur trioxide of $C_{12-18}$ monoolefins having a terminal or internal double bond and subsequent alkaline or acidic hydrolysis of the sulfonation products.

Alk(en)yl sulfates. Preferred alk(en)yl sulfates are the alkali and especially the sodium salts of the sulfuric acid half-esters of the $C_{12}$-$C_{18}$ fatty alcohols, for example, from coconut butter alcohol, tallow alcohol, lauryl, myristyl, cetyl or stearyl alcohol or from $C_8$-$C_{20}$ oxo alcohols and those half-esters of secondary alcohols of these chain lengths. Alk(en)yl sulfates of the cited chain lengths that comprise a synthetic straight chain alkyl group manufactured petrochemically are also preferred. The $C_{12}$-$C_{16}$ alkyl sulfates and $C_{12}$-$C_{15}$ alkyl sulfates as well as $C_{14}$-$C_{15}$ alkyl sulfates and $C_{14}$-$C_{16}$ alkyl sulfates are particularly preferred on the grounds of laundry performance. The 2,3-alkyl sulfates, which can be obtained from Shell Oil Company under the trade name DAN™, are also suitable anionic surfactants.

Alk(en)yl ether sulfates. Sulfuric acid mono-esters derived from straight-chained or branched $C_7$-$C_{21}$ alcohols ethoxylated with 1 to 6 moles ethylene oxide are also suitable, such as 2-methyl-branched $C_9$-$C_{11}$ alcohols with an average of 3.5 mol ethylene oxide (EO) or $C_{12}$-$C_{18}$ fatty alcohols with 1 to 4 EO.

Ester sulfonates. The esters of alpha-sulfo fatty acids (ester sulfonates), e.g., the alpha-sulfonated methyl esters of hydrogenated coco-, palm nut- or tallow acids are likewise suitable.

Soaps. Soaps, in particular, can be considered as further anionic surfactants. Saturated fatty acid soaps are particularly suitable, such as the salts of lauric acid, myristic acid, palmitic acid, stearic acid, hydrogenated erucic acid and behenic acid, and especially soap mixtures derived from natural fatty acids such as coconut oil fatty acid, palm kernel oil fatty acid or tallow fatty acid. Those soap mixtures are particularly preferred that are composed of 50 to 100 wt. % of saturated $C_{12}$-$C_{24}$ fatty acid soaps and 0 to 50 wt. % of oleic acid soap.

Ether carboxylic acids. A further class of anionic surfactants is that of the ether carboxylic acids, obtainable by treating fatty alcohol ethoxylates with sodium chloroacetate in the presence of basic catalysts. They have the general formula: $RO(CH_2CH_2O)_pCH_2COOH$ with $R=C_1-C_{18}$ and p=0.1 to 20. Ether carboxylic acids are insensitive to water hardness and possess excellent surfactant properties.

Non-Ionic Surfactants

Alkohol alkoxylates. The added nonionic surfactants are preferably alkoxylated and/or propoxylated, particularly primary alcohols having preferably 8 to 18 carbon atoms and an average of 1 to 12 mol ethylene oxide (EO) and/or 1 to 10 mol propylene oxide (PO) per mol alcohol. $C_8-C_{16}$-Alcohol alkoxylates, advantageously ethoxylated and/or propoxylated $C_{10}-C_{15}$-alcohol alkoxylates, particularly $C_{12}-C_{14}$ alcohol alkoxylates, with an ethoxylation degree between 2 and 10, preferably between 3 and 8, and/or a propoxylation degree between 1 and 6, preferably between 1.5 and 5, are particularly preferred. The cited degrees of ethoxylation and propoxylation constitute statistical average values that can be a whole or a fractional number for a specific product. Preferred alcohol ethoxylates and propoxylates have a narrowed homolog distribution (narrow range ethoxylates/propoxylates, NRE/NRP). In addition to these nonionic surfactants, fatty alcohols with more than 12 EO can also be used. Examples of these are (tallow) fatty alcohols with 14 EO, 16 EO, 20 EO, 25 EO, 30 EO or 40 EO.

Alkylglycosides (APG®). Furthermore, as additional nonionic surfactants, alkyl glycosides that satisfy the general Formula $RO(G)_x$, can be added, e.g., as compounds, particularly with anionic surfactants, in which R means a primary linear or methyl-branched, particularly 2-methyl-branched, aliphatic group containing 8 to 22, preferably 12 to 18 carbon atoms and G stands for a glycose unit containing 5 or 6 carbon atoms, preferably for glucose. The degree of oligomerization x, which defines the distribution of monoglycosides and oligoglycosides, is any number between 1 and 10, preferably between 1.1 and 1.4.

Fatty acid ester alkoxylates. Another class of preferred nonionic surfactants, which are used either as the sole nonionic surfactant or in combination with other non-ionic surfactants, in particular, together with alkoxylated fatty alcohols and/or alkyl glycosides, are alkoxylated, preferably ethoxylated or ethoxylated and propoxylated fatty acid alkyl esters preferably containing 1 to 4 carbon atoms in the alkyl chain, more particularly the fatty acid methyl esters which are described, for example, in Japanese Patent Application JP-A-58/217598 or which are preferably produced by the process described in International Patent Application WO-A-90/13533. Methyl esters of $C_{12}-C_{18}$ fatty acids containing an average of 3 to 15 EO, particularly containing an average of 5 to 12 EO, are particularly preferred.

Amine oxides. Nonionic surfactants of the amine oxide type, for example, N-coco alkyl-N,N-dimethylamine oxide and N-tallow alkyl-N,N-dihydroxyethylamine oxide, and the fatty acid alkanolamides may also be suitable. The quantity in which these nonionic surfactants are used is preferably no more than the quantity in which the ethoxylated fatty alcohols are used and, particularly no more than half that quantity.

Gemini surfactants. The so-called gemini surfactants can be considered as further surfactants. Generally speaking, such compounds are understood to mean compounds that have two hydrophilic groups and two hydrophobic groups per molecule. As a rule, these groups are separated from one another by a "spacer". The spacer is usually a hydrocarbon chain that is intended to be long enough such that the hydrophilic groups are a sufficient distance apart to be able to act independently of one another. These types of surfactants are generally characterized by an unusually low critical micelle concentration and the ability to strongly reduce the surface tension of water. In exceptional cases, however, not only dimeric but also trimeric surfactants are meant by the term gemini surfactants. Suitable gemini surfactants are, for example, sulfated hydroxy mixed ethers according to German Patent Application DE 4321022 A1 or dimer alcohol bis- and trimer alcohol tris sulfates and ether sulfates according to International Patent Application WO 96/23768 A1. Blocked end group dimeric and trimeric mixed ethers according to German Patent Application DE 19513391 A1 are especially characterized by their bifunctionality and multifunctionality. Gemini polyhydroxyfatty acid amides or polyhydroxyfatty acid amides, such as those described in International Patent Applications WO 95/19953 A1, WO 95/19954 A1 and WO 95/19955 A1 can also be used.

Cationic Surfactants

Tetraalkyl ammonium salts. Cationically active surfactants comprise the hydrophobic high molecular group required for the surface activity in the cation by dissociation in aqueous solution. A group of important representatives of the cationic surfactants are the tetraalkyl ammonium salts of the general formula: $(R^1R^2R^3R^4N^+) X^-$. Here $R^1$ stands for $C_1-C_8$ alk(en)yl, $R^2$, $R^3$ and $R^4$, independently of each other, for alk(en)yl radicals having 1 to 22 carbon atoms. X is a counter ion, preferably selected from the group of the halides, alkyl sulfates and alkyl carbonates. Cationic surfactants, in which the nitrogen group is substituted with two long acyl groups and two short alk(en)yl groups, are particularly preferred.

Esterquats. A further class of cationic surfactants particularly useful as co-surfactants for the present invention is represented by the so-called esterquats. Esterquats are generally understood to be quaternised fatty acid triethanolamine ester salts. These are known compounds which can be obtained by the relevant methods of preparative organic chemistry. Reference is made in this connection to International patent application WO 91/01295 A1, according to which triethanolamine is partly esterified with fatty acids in the presence of hypophosphorous acid, air is passed through the reaction mixture and the whole is then quaternised with dimethyl sulphate or ethylene oxide. In addition, German patent DE 4308794 C1 describes a process for the production of solid esterquats in which the quaternisation of triethanolamine esters is carried out in the presence of suitable dispersants, preferably fatty alcohols.

Typical examples of esterquats suitable for use in accordance with the invention are products of which the acyl component derives from monocarboxylic acids corresponding to formula RCOOH in which RCO is an acyl group containing 6 to 10 carbon atoms, and the amine component is triethanolamine (TEA). Examples of such monocarboxylic acids are caproic acid, caprylic acid, capric acid and technical mixtures thereof such as, for example, so-called head-fractionated fatty acid. Esterquats of which the acyl component derives from monocarboxylic acids containing 8 to 10 carbon atoms, are preferably used. Other esterquats are those of which the acyl component derives from dicarboxylic acids like malonic acid, succinic acid, maleic acid, fumaric acid, glutaric acid, sorbic acid, pimelic acid, azelaic acid, sebacic acid and/or dodecanedioic acid, but preferably adipic acid. Overall, esterquats of which the acyl component derives from mixtures of monocarboxylic acids containing 6 to 22 carbon atoms, and adipic acid are preferably used. The molar ratio of mono and dicarboxylic acids in the final esterquat may be in the range from 1:99 to 99:1 and is preferably in the range from 50:50 to 90:10 and more particularly in the range from 70:30 to 80:20. Besides the quaternised fatty acid triethanolamine ester salts, other suitable esterquats are quaternized ester salts of mono/dicarboxylic acid mixtures with diethanolalkyamines or 1,2-dihydroxypropyl dialkylamines. The esterquats may be obtained both from fatty acids and from the corresponding triglycerides in admixture with the corresponding dicarboxylic acids. One such process, which is intended to be representative of the relevant prior art, is proposed in European patent EP 0750606 B1. To produce the quaternised esters, the mixtures of mono- and dicarboxylic acids and the triethanolamine—based on the available carboxyl functions—may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9.

Amphoteric or Zwitterionic Co-Surfactants

Betaines. Amphoteric or ampholytic surfactants possess a plurality of functional groups that can ionize in aqueous solution and thereby—depending on the conditions of the medium—lend anionic or cationic character to the compounds (see DIN 53900, July 1972). Close to the isoelectric point (around pH 4), the amphoteric surfactants form inner salts, thus becoming poorly soluble or insoluble in water. Amphoteric surfactants are subdivided into ampholytes and betaines, the latter existing as zwitterions in solution. Ampholytes are amphoteric electrolytes, i.e. compounds that possess both acidic as well as basic hydrophilic groups and therefore behave as acids or as bases depending on the conditions. Especially betaines are known surfactants which are mainly produced by carboxyalkylation, preferably carboxymethylation, of amine compounds. The starting materials are preferably condensed with halocarboxylic acids or salts thereof, more particularly sodium chloroacetate, one mole of salt being formed per mole of betaine. The addition of unsaturated carboxylic acids, such as acrylic acid for example, is also possible. Examples of suitable betaines are the carboxy alkylation products of secondary and, in particular, tertiary amines which correspond to formula $R^1R^2R^3N$—$(CH_2)_q COOX$ where $R^1$ is a an alkyl radical having 6 to 22 carbon atoms, $R^2$ is hydrogen or an alkyl group containing 1 to 4 carbon atoms, $R^3$ is an alkyl group containing 1 to 4 carbon atoms, q is a number of 1 to 6 and X is an alkali and/or alkaline earth metal or ammonium. Typical examples are the carboxymethylation products of hexylmethylamine, hexyldimethylamine, octyldimethylamine, decyldimethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallowalkyldimethylamine and their technical mixtures, and particularly dodecyl methylamine, dodecyl dimethylamine, dodecyl ethylmethylamine and technical mixtures thereof. The commercially available products include Dehyton® AB (Cognis Deutschland GmbH & Co., KG)

Alkylamido betaines. Other suitable betaines are the carboxyalkylation products of amidoamines corresponding to formula $R^1CO(R^3)(R^4)$—$NH$—$(CH_2)_p$—$N$—$(CH_2)_q COOX$ in which $R^1CO$ is an aliphatic acyl radical having 6 to 22 carbon atoms and 0 or 1 to 3 double bonds, $R^2$ is hydrogen or an alkyl radical having 1 to 4 carbon atoms, $R^3$ is an alkyl radical having 1 to 4 carbon atoms, p is a number from 1 to 6, q is a number from 1 to 3 and X is an alkali and/or alkaline earth metal or ammonium. Typical examples are reaction products of fatty acids having 6 to 22 carbon atoms, like for example caproic acid, caprylic acid, caprinic acid, lauric acid, myristic acid, palmitic acid, palmoleic acid, stearic acid, isostearic acid, oleic acid, elaidic acid, petroselinic acid, linolic acid linoleic acid, elaeostearic acid, arachidonic acid, gadoleic acid, behenic acid, erucic acid and their technical mixtures with N,N-dimethylaminoethylamine, N,N-dimethylaminopropylamine, N,N-diethylaminoethylamine and N,N-diethylaminopropylamine, which are condensed with sodium chloroacetate. The commercially available products include Dehyton® K and Dehyton® PK (Cognis Deutschland GmbH & Co., KG) as well as Tego® Betaine (Goldschmidt).

Imidazolines. Other suitable starting materials for the betaines to be used for the purposes of the invention are imidazolines. These substances are also known and may be obtained, for example, by cyclizing condensation of 1 or 2 moles of $C_6$-$C_{22}$ fatty acids with polyfunctional amines, such as for example aminoethyl ethanolamine (AEEA) or diethylenetriamine. The corresponding carboxyalkylation products are mixtures of different open-chain betaines. Typical examples are condensation products of the above-mentioned fatty acids with AEEA, preferably imidazolines based on lauric acid, which are subsequently betainised with sodium chloroacetate. The commercially available products include Dehyton® G (Cognis Deutschland GmbH & Co., KG)

The amount of surfactant comprised in the inventive compositions is advantageously 0.1 wt. % to 90 wt. %, particularly 10 wt. % to 80 wt. % and particularly preferably 20 wt. % to 70 wt.-%.

Organic Solvents

Detergent compositions according to the present invention may comprise organic solvents, preferably those miscible with water. Polydiols, ethers, alcohols, ketones, amides and/or esters are preferably used as the organic solvent for this in amounts of 0 to 90 wt. %, preferably 0.1 to 70 wt. %, particularly 0.1 to 60 wt. %. Low molecular weight polar substances, such as for example, methanol, ethanol, propylene carbonate, acetone, acetonylacetone, diacetone alcohol, ethyl acetate, 2-propanol, ethylene glycol, propylene glycol, glycerin, diethylene glycol, dipropylene glycol monomethyl ether and dimethylformamide or their mixtures are preferred.

Enzymes

Suitable enzymes include, in particular, those from the classes of hydrolases, such as proteases, esterases, lipases or lipolytic enzymes, amylases, cellulases or other glycosyl hydrolases and mixtures thereof. In the wash, all these hydrolases contribute to removing stains such as protein, fat or starchy stains and against graying. Moreover, cellulases and other glycosyl hydrolases can contribute to increased softness of the textile and to color retention by removing pilling and micro fibrils. Oxidoreductases can also be added to the bleaches or to inhibit the color transfer. Enzymatic active materials obtained from bacterial sources or fungi such as *bacillus subtilis, bacillus licheniformis, streptomyceus griseus* and *humicola insolens* are particularly well suited. Proteases of the subtilisin type and particularly proteases that are obtained from *bacillus lentus* are preferably used. Here, mixtures of enzymes are of particular interest, for example, proteases and amylases or proteases and lipases or lipolytic enzymes or proteases and cellulases or cellulases and lipase or lipolytic enzymes or proteases, amylases and lipases or lipolytic enzymes or proteases, lipases or lipolytic enzymes and cellulases, in particular, however proteases and/or lipase-containing mixtures or mixtures with lipolytic enzymes. Examples of such lipolytic enzymes are the known cutinases. Peroxidases or oxidases have also proved to be suitable in certain cases. The suitable amylases particularly include .alpha.-amylases, iso-amylases, pullulanases and pectinases. Cellobiohydrolases, endoglucanases and .beta.-glucosidases or mixtures thereof, which are also known as cellobiases, are preferred cellulases. As the different cellulase types differ in their CMCase and avicelase activities, the required activities can be adjusted by controlled mixtures of the cellulases. The content of the enzymes or enzyme mixtures may be, for example, about 0.1 to 5% by weight and is preferably 0.1 to about 3% by weight.

Soil Repellents

In addition, the compositions can also comprise components that positively influence the oil and fat removal from textiles during the wash (so-called soil repellents). This effect is particularly noticeable when a textile is dirty and had been previously already washed several times with an inventive detergent that comprised this oil- or fat-removing component. The preferred oil and fat removing components include, for example, nonionic cellulose ethers such as methyl cellulose and methyl hydroxypropyl cellulose with a content of methoxy groups of 15 to 30 wt. % and hydroxypropoxy groups of 1 to 15 wt. %, each based on the nonionic cellulose ether, as well as polymers of phthalic acid and/or terephthalic acid or their derivatives known from the prior art, particularly polymers of ethylene terephthalates and/or polyethylene glycol terephthalates or anionically and/or nonionically modified derivatives thereof. From these, the sulfonated derivatives of the phthalic acid polymers and the terephthalic acid polymers are particularly preferred.

Foam Inhibitors

Especially when used in automatic washing processes, but also for specific cleaning purposes it can be advantageous to add conventional foam inhibitors to the compositions. Suitable foam inhibitors include for example, soaps of natural or synthetic origin, which have a high content of $C_{18}$-$C_{24}$ fatty acids. Suitable non-surface-active types of foam inhibitors are, for example, organopolysiloxanes and mixtures thereof with microfine, optionally silanised silica and also paraffins, waxes, microcrystalline waxes and mixtures thereof with silanised silica or bis-stearyl ethylenediamide. Mixtures of various foam inhibitors, for example, mixtures of silicones, paraffins or waxes, are also used with advantage. Preferably, the foam inhibitors, especially silicone-containing and/or paraffin-containing foam inhibitors, are loaded onto a granular, water-soluble or dispersible carrier material. Especially in this case, mixtures of paraffins and bis-stearylethylene diamides are preferred.

Sequestrants

The salts of polyphosphonic acid can be considered as sequestrants or as stabilizers, particularly for peroxy compounds and enzymes, which are sensitive towards heavy metal ions. Here, the sodium salts of, for example, 1-hydroxyethane-1,1-diphosphonate, diethylenetriamine pentamethylene phosphonate or ethylenediamine tetramethylene phosphonate are used in amounts of 0.1 to 5 wt. %.

Thickeners

The compositions can also comprise common thickeners and anti-deposition compositions as well as viscosity regulators such as polyacrylates, polycarboxylic acids, polysaccharides and their derivatives, polyurethanes, polyvinyl pyrrolidones, castor oil derivatives, polyamine derivatives such as quaternized and/or ethoxylated hexamethylenediamines as well as any mixtures thereof. Preferred compositions have a viscosity below 10,000 mPa*s, measured with a Brookfield viscosimeter at a temperature of 20° C. and a shear rate of 50 $min^{-1}$.

Personal Care Compositions

The perfume compositions of the present invention are also useful for perfuming various personal care compositions which are brought into contact with human skin. A prominent example is of course a deodorant, but also shampoos, shower gels or body lotions represent suitable applications for the compositions. These products may contain the same anionic, non-ionic, cationic and/or amphoteric surfactants which were already described above. In addition they may comprise as further additives such as oil bodies, emulsifiers, superfatting agents, pearlising waxes, consistency factors, polymers, silicone compounds, waxes, stabilizers, antidandruff agents, biogenic agents, film formers, swelling agents, hydrotropes, preservatives, solubilizers, complexing agents, reducing agents, alkalising agents, perfume oils, dyes and the like.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:
- products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
- $C_{12/18}$ fatty acid monoesters and diesters of addition products of 1 to 30 mol ethylene oxide onto glycerol;
- glycerol mono- and diesters and sorbitan mono- and diesters of saturated and unsaturated fatty acids containing 6 to 22 carbon atoms and ethylene oxide addition products thereof;
- addition products of 15 to 60 mol ethylene oxide onto castor oil and/or hydrogenated castor oil;
- polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
- addition products of 2 to 15 mol ethylene oxide onto castor oil and/or hydrogenated castor oil;
- partial esters based on linear, branched, unsaturated or saturated $C_{6122}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
- mono-, di and trialkyl phosphates and mono-, di- and/or tri-PEG-alkyl phosphates and salts thereof;
- wool wax alcohols;
- polysiloxane/polyalkyl polyether copolymers and corresponding derivatives;
- mixed esters of pentaerythritol, fatty acids, citric acid and fatty alcohol and/or mixed esters of $C_{6-22}$ fatty acids, methyl glucose and polyols, preferably glycerol or polyglycerol,
- polyalkylene glycols and
- glycerol carbonate.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Consistency Factors

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat®(BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar®CBS, Jaguar®C17, Jaguar®C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxyystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Stabilizers

Metal salts of fatty acids such as, for example, magnesium, aluminium and/or zinc stearate or ricinoleate may be used as stabilizers.

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, polyphenols, flavonoids, AHA acids, amino acids, ceramides, pseudoceramides, essential oils, plant extracts, for example extracts of *Ginkgo biloba, Oleacea europensis, Glyzyrrhiza glabra, Vaccinium myrtillus, Trifolium pratense, Litchi sinensis, Vitis, vinifera, Brassica oleracea, Punica granatum, Petroselinium crispum, Centella asiatica, Passiflora incarnata, Medicago sativa, Melissa officinalis, Valeriana officinalis, Castanea sativa, Salix alba* and *Hapagophytum procumbens* extract, and vitamin complexes.

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenyl, 2,2'-methylenebis(6-bromo-4-chloro-phenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Additional Odour Absorbers

Suitable odour absorbers are substances which are able to absorb and largely retain odourforming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum.

Antiperspirant Active Ingredients

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-

(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Hydrotropes

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Complexing Agents

The complexing agents used may be selected from EDTA, NTA, phosphonic acids, Triton B, turpinal and phenacetin. In addition, reducing agents such as, for example, ascorbic acid, sodium sulfate, sodium thiosulfate and the like may be present. Suitable alkalizing agents are ammonia, monoethanolamines, (L) arginine, AMP, etc.

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, alphaisomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS(C.I. 69800) and madder lake (C.I. 58000). Luminol may also be present as a luminescent dye. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular composition. The compositions may be produced by standard hot or cold processes.

EXAMPLES

In the following veracious perfume compositions were tested in order to show that the compositions according to the invention are active in fighting very different malodours. Table A shows the composition of the test compounds:

TABLE A

| Composition of perfume compounds according to the invention - all values as % b.w. | | | | | |
|---|---|---|---|---|---|
| Compound | A | B | C | D | E |
| Citronella oil | — | — | — | 2 | 2 |
| Lavender oil | 20 | 10 | — | — | — |

TABLE A-continued

Composition of perfume compounds according to the invention - all values as % b.w.

| Compound | A | B | C | D | E |
|---|---|---|---|---|---|
| *Litsea cubeba* oil | 0.5 | 2 | 5 | 10 | — |
| Palmarosa oil | — | — | 5 | 4 | 1.5 |
| Petit grain oil | 0.5 | 2 | 7 | 14 | 25 |
| Peppermint oil | — | 10 | 10 | 5 | 4.5 |
| Pine oil | — | — | — | — | 2 |
| Triethyl citrate | | | ad 100 | | |

Example 1

The compositions A to E were added to a standard unperfumed liquid manual dish washing composition in amounts of 0.2% b.w. each. Each 2.0 g of the perfumed compositions A to E thus obtained were placed on a Petri dish and put into a 7 l air filled sniffer bag together with 1 µl kitchen malodour concentrate. 15 expert panellists evaluated the samples with regard to perfume intensity and malodour intensity on a scale from (1)=odourless to (9)=very strong. The results are compiled in Table 1. The values correspond to the arithmetic means of the tests. The examples C1 and to C2 refer to an unperfumed composition and a standard kitchen malodour composition serving for comparison.

TABLE 1

Perfume and malodour intensities for kitchen smell

| Composition | A1 | B1 | B3 | B4 | B5 | C1 | C2 |
|---|---|---|---|---|---|---|---|
| Mean perfume intensity | 5.57 | 5.73 | 5.40 | 5.27 | 5.36 | 1.14 | 1.00 |
| Mean malodour intensity | 2.40 | 2.27 | 2.00 | 1.73 | 2.07 | 4.86 | 6.00 |

Example 2

The compositions A to E were added to a standard unperfumed liquid manual dish washing composition in amounts of 0.2% b.w. each. Then, cotton balls were left to take of cigarette smoke. Each 2.0 g of the perfumed compositions A to E were placed on a Petri dish and put into a 7 l air filled sniffer bag together with 4 of said smoke flavoured cotton balls. 15 expert panellists evaluated the samples with regard to perfume intensity and malodour intensity on a scale from (1)=odourless to (9)=very strong. The results are compiled in Table 2. The values correspond to the arithmetic means of the tests. The examples C1 and to C2 refer to an unperfumed composition and a standard smoke malodour composition serving for comparison.

TABLE 2

Perfume and malodour intensities for smoke smell

| Composition | A | B | C | D | E | C1 | C2 |
|---|---|---|---|---|---|---|---|
| Mean perfume intensity | 4.19 | 3.80 | 3.88 | 3.20 | 3.07 | 1.00 | 1.00 |
| Mean malodour intensity | 4.43 | 4.31 | 4.25 | 5.07 | 5.07 | 5.40 | 7.00 |

Example 3

The compositions A to E were added to a standard unperfumed liquid manual dish washing composition in amounts of 0.2% b.w. each. Each 2.0 g of the perfumed compositions A to E thus obtained were placed on a Petri dish and put into a 7 l air filled sniffer bag together with 1 µl bathroom malodour concentrate. 15 expert panellists evaluated the samples with regard to perfume intensity and malodour intensity on a scale from (1)=odourless to (9)=very strong. The results are compiled in Table 3. The values correspond to the arithmetic means of the tests. The examples C1 and to C2 refer to an unperfumed composition and a standard bathroom malodour composition serving for comparison.

TABLE 3

Perfume and malodour intensities for bathroom smell

| Composition | A | B | C | D | E | C1 | C2 |
|---|---|---|---|---|---|---|---|
| Mean perfume intensity | 4.31 | 4.56 | 3.94 | 4.19 | 3.50 | 1.00 | 1.00 |
| Mean malodour intensity | 2.69 | 3.13 | 3.31 | 2.67 | 2.44 | 4.79 | 6.00 |

Example 4

The compositions A to E were added to a standard unperfumed all-purpose cleaning composition in amounts of 0.2% b.w. each. Each 2.0 g of the perfumed compositions A to E thus obtained were placed on a Petri dish and put into a 7 l air filled sniffer bag together with 1 µl kitchen malodour concentrate. 15 expert panellists evaluated the samples with regard to perfume intensity and malodour intensity on a scale from (1)=odourless to (9)=very strong. The results are compiled in Table 4. The values correspond to the arithmetic means of the tests. The examples C1 and to C2 refer to an unperfumed composition and a standard kitchen malodour composition serving for comparison.

TABLE 4

Perfume and malodour intensities for kitchen smell

| Composition | A | B | C | D | E | C1 | C2 |
|---|---|---|---|---|---|---|---|
| Mean perfume intensity | 5.31 | 5.23 | 5.69 | 5.92 | 5.31 | 1.83 | 1.00 |
| Mean malodour intensity | 1.92 | 1.31 | 1.26 | 1.33 | 1.42 | 3.22 | 6.00 |

Example 5

The compositions A to E were added to a standard unperfumed all-purpose cleaning composition in amounts of 0.2% b.w. each. Then, cotton balls were left to take of cigarette smoke. Each 2.0 g of the perfumed compositions A to E were placed on a Petri dish and put into a 7 l air filled sniffer bag together with 4 of said smoke flavoured cotton balls. 15 expert panellists evaluated the samples with regard to perfume intensity and malodour intensity on a scale from (1)=odourless to (9)=very strong. The results are compiled in Table 5. The values correspond to the arithmetic means of the tests. The examples C1 and to C2 refer to an upperfumed composition and a standard smoke malodour composition serving for comparison.

TABLE 5

Perfume and malodour intensities for smoke smell

| Composition | A | B | C | D | E | C1 | C2 |
|---|---|---|---|---|---|---|---|
| Mean perfume intensity | 3.07 | 2.67 | 3.00 | 3.60 | 2.43 | 1.14 | 1.00 |
| Mean malodour intensity | 5.36 | 5.86 | 5.43 | 4.79 | 5.36 | 5.93 | 7.00 |

Example 6

The compositions A to E were added to a standard unperfumed all-purpose cleaning composition in amounts of 0.2% b.w. each. Each 2.0 g of the perfumed compositions A to E thus obtained were placed on a Petri dish and put into a 7 l air filled sniffer bag together with 1 μl bathroom malodour concentrate. 15 expert panellists evaluated the samples with regard to perfume intensity and malodour intensity on a scale from (1)=odourless to (9)=very strong. The results are compiled in Table 6. The values correspond to the arithmetic means of the tests. The examples C1 and to C2 refer to an unperfumed composition and a standard bathroom malodour composition serving for comparison.

TABLE 6

Perfume and malodour intensities for bathroom smell

| Composition | A | B | C | D | E | C1 | C2 |
|---|---|---|---|---|---|---|---|
| Mean perfume intensity | 4.73 | 4.20 | 3.67 | 4.46 | 4.79 | 1.14 | 1.00 |
| Mean malodour intensity | 3.16 | 3.33 | 3.13 | 2,73 | 3.46 | 4.46 | 6.00 |

Example 7

The compositions A to E were added in amounts of 0.2% b.w. each to a standard liquid manual dish washing composition already comprising 0.02% b.w. limonene as the base perfume. Each 2.0 g of the perfumed compositions A to E thus obtained were placed on a Petri dish and put into a 7 l air filled sniffer bag together with 1 μl kitchen malodour concentrate. 15 expert panellists evaluated the samples with regard to perfume intensity and malodour intensity on a scale from (1)=odourless to (9)=very strong. The results are compiled in Table 7. The values correspond to the arithmetic means of the tests. The examples C1 to C3 refer to the standard perfumed composition, an unperfumed composition and a standard kitchen malodour composition serving for comparison.

TABLE 7

Perfume and malodour intensities for kitchen smell

| Composition | A | B | C | D | E | C1 | C2 | C3 |
|---|---|---|---|---|---|---|---|---|
| Mean perfume intensity | 6.00 | 5.64 | 5.69 | 6.21 | 4,54 | 5.00 | 1.15 | 1.00 |
| Mean malodour intensity | 1.23 | 1.57 | 2.07 | 2.07 | 1.93 | 2.69 | 4.92 | 6.00 |

Example 8

The compositions A to E were added in amounts of 0.2% b.w. each to a standard liquid manual dish washing composition already comprising 0.02% b.w. limonene as the base perfume. Then, cotton balls were left to take of cigarette smoke. Each 2.0 g of the perfumed compositions A to E were placed on a Petri dish and put into a 7 l air filled sniffer bag together with 4 of said smoke flavoured cotton balls. 15 expert panellists evaluated the samples with regard to perfume intensity and malodour intensity on a scale from (1)=odourless to (9)=very strong. The results are compiled in Table 8. The values correspond to the arithmetic means of the tests. The examples C1 to C3 refer to the standard perfumed composition, an unperfumed composition and a standard kitchen malodour composition serving for comparison.

TABLE 8

Perfume and malodour intensities for smoke smell

| Composition | A | B | C | D | E | C1 | C2 | C3 |
|---|---|---|---|---|---|---|---|---|
| Mean perfume intensity | 3.15 | 5.21 | 4.57 | 4.50 | 4.08 | 3.77 | 1.23 | 1.00 |
| Mean malodour intensity | 4.10 | 3.17 | 2.86 | 3.00 | 3.70 | 4.36 | 5.23 | 7.00 |

Example 9

The compositions A to E were added in amounts of 0.2% b.w. each to a standard liquid manual dish washing composition already comprising 0.02% b.w. limonene as the base perfume. Each 2.0 g of the perfumed compositions A to E thus obtained were placed on a Petri dish and put into a 7 l air filled sniffer bag together with 1 μl bathroom malodour concentrate. 15 expert panellists evaluated the samples with regard to perfume intensity and malodour intensity on a scale from (1)=odourless to (9)=very strong. The results are compiled in Table 9. The values correspond to the arithmetic means of the tests. The examples C1 to C3 refer to the standard perfumed composition, an unperfumed composition and a standard kitchen malodour composition serving for comparison.

TABLE 9

Perfume and malodour intensities for bathroom smell

| Composition | A | B | C | D | E | C1 | C2 | C3 |
|---|---|---|---|---|---|---|---|---|
| Mean perfume intensity | 5.14 | 4.60 | 5.00 | 5.21 | 4.20 | 4.93 | 1.43 | 1.00 |
| Mean malodour intensity | 2.50 | 2.07 | 2.36 | 2.33 | 2.70 | 2.93 | 4.27 | 6.00 |

Example 10

The compositions A to E were added in amounts of 0.2% b.w. each to a standard all-purpose cleaner washing composition already comprising 0.02% b.w. limonene as the base perfume. Each 2.0 g of the perfumed compositions A to E thus obtained were placed on a Petri dish and put into a 7 l air filled sniffer bag together with 1 μl kitchen malodour concentrate. 15 expert panellists evaluated the samples with regard to perfume intensity and malodour intensity on a scale from (1)=odourless to (9)=very strong. The results are compiled in Table 10. The values correspond to the arithmetic means of the tests. The examples F1 to F3 refer to the standard perfumed composition, an unperfumed composition and a standard kitchen malodour composition serving for comparison.

TABLE 10

Perfume and malodour intensities for kitchen smell

| Composition | A | B | C | D | E | F1 | F2 | F3 |
|---|---|---|---|---|---|---|---|---|
| Mean perfume intensity | 5.15 | 5.43 | 4.93 | 4.86 | 5.40 | 4.87 | 1.21 | 1.00 |
| Mean malodour intensity | 2.21 | 1.93 | 1.86 | 1.79 | 1.43 | 2.43 | 4.67 | 6.00 |

Example 11

The compositions A to E were added in amounts of 0.2% b.w. each to a standard all-purpose cleaning composition already comprising 0.02% b.w. limonene as the base perfume. Then, cotton balls were left to take of cigarette smoke. Each 2.0 g of the perfumed compositions A to E were placed on a Petri dish and put into a 7 l air filled sniffer bag together with 4 of said smoke flavoured cotton balls. 15 expert panellists evaluated the samples with regard to perfume intensity and malodour intensity on a scale from (1)=odourless to (9)=very strong. The results are compiled in Table 11. The values correspond to the arithmetic means of the tests. The examples F1 to F3 refer to the standard perfumed composition, an unperfumed composition and a standard kitchen malodour composition serving for comparison.

TABLE 11

Perfume and malodour intensities for smoke smell

| Composition | A | B | C | D | E | F1 | F2 | F3 |
|---|---|---|---|---|---|---|---|---|
| Mean perfume intensity | 3.86 | 4.21 | 2.85 | 2.69 | 3.29 | 3.92 | 1.08 | 1.00 |
| Mean malodour intensity | 5.00 | 3.75 | 5.21 | 5.17 | 5.15 | 5.50 | 6.29 | 7.00 |

Example 12

The compositions A to E were added in amounts of 0.2% b.w. each to a standard all-purpose cleaning composition already comprising 0.02% b.w. limonene as the base perfume. Each 2.0 g of the perfumed compositions A to E thus obtained were placed on a Petri dish and put into a 7 l air filled sniffer bag together with 1 µl bathroom malodour concentrate. 15 expert panellists evaluated the samples with regard to perfume intensity and malodour intensity on a scale from (1)=odourless to (9)=very strong. The results are compiled in Table 12. The values correspond to the arithmetic means of the tests. The examples F1 to F3 refer to the standard perfumed composition, an unperfumed composition and a standard kitchen malodour composition serving for comparison.

TABLE 12

Perfume and malodour intensities for bathroom smell

| Composition | A | B | C | D | E | F1 | F2 | F3 |
|---|---|---|---|---|---|---|---|---|
| Mean perfume intensity | 5.08 | 5.15 | 4.71 | 5.00 | 4.92 | 4.62 | 1.71 | 1.00 |
| Mean malodour intensity | 2.71 | 2.38 | 2.93 | 2.62 | 1.85 | 3.14 | 4.69 | 6.00 |

Example 13

The following Table 13 provides examples for typical deodorant compositions comprising the perfume compositions according to the present invention.

TABLE 13

Deodorant compositions

| Composition | 1 | 2 | 3 | 4 | 5 | 6 | 7 | 8 |
|---|---|---|---|---|---|---|---|---|
| Alumina chloro hydrate | 25 | 25 | 25 | 25 | 25 | 28 | 28 | 25 |
| Cetearyl alcohol | 1 | 1 | 2 | 1 | 2 | 1 | 1 | — |
| Propylheptyl caprylate | 1 | 1 | — | — | 2 | — | 1 | — |
| Dicaprylyl carbonate | 1 | — | 1 | 2 | — | — | 1 | — |
| Dicaprylyl ether | — | 1 | 1 | — | — | — | — | — |
| Dimethicone | 0.5 | 0.5 | 1 | 1 | 0.5 | 0.5 | 0.5 | — |
| Polyquart 37 | 3 | 3 | 2 | 3 | 2 | 1 | 1 | 6.0 |
| Glycerol | — | — | — | — | — | — | — | 5.0 |
| Perfume composition A | 0.02 | 0.02 | 0.02 | 0.02 | 0.02 | 0.02 | 0.02 | 0.02 |
| Water | Ad 100 | | | | | | | |

Example 14

The following Table 14 provides examples for typical manual dishwashing compositions comprising the perfume compositions according to the present invention.

TABLE 14

Manual dishwashing compositions

| Composition | 1 | 2 | 3 | 4 | 5 | 6 |
|---|---|---|---|---|---|---|
| Sodium octyl sulfate | 15 | — | — | — | — | — |
| Sodium lauryl sulfate | — | 15 | — | — | — | — |
| Sodium laureth-2 sulfate | — | 15 | 18 | 22 | 24 | 22 |
| Sodium dioctyl sulfosuccinate | — | — | 7 | — | — | 4 |
| Coco glucosides | 6 | 6 | 6 | 6 | 8 | 4 |
| Cocamidopropylbetaine | 4 | 4 | 4 | 4 | 3 | 4 |
| Silk protein hydrolyzate | — | — | — | — | 1 | 1 |
| Bisabolol | 0.3 | 0.3 | 0.3 | 0.3 | 0.3 | 0.3 |
| Perfume composition F | 0.02 | 0.02 | 0.02 | 0.02 | 0.02 | 0.02 |
| Water | Ad 100 | | | | | |

The invention claimed is:

1. A detergent composition or personal care composition comprising:
   (A) a perfume composition comprising
   (a) about 0.1 to about 40 wt % petit grain oil,
   (b) about 99.9 to about 60 wt % of a hydroxy carboxylic acid ester selected from the group consisting of $C_1$-$C_4$ alkyl esters of citric acid, malic acid and/or tartaric acid, (c) 1 to about 20 wt % of a terpene and
(d) 1 to about 25 wt % essential oil selected from the group consisting of citronella oil, lavender oil, litsea cubeba oil, palmarosa oil, peppermint oil, pine oil and their mixtures; and
(B) a surfactant in the amount of from 0.1 to 90 wt % based on the total weight of the detergent composition or personal care composition.

2. The detergent composition or personal care composition of claim 1, wherein said terpene is either limonene or menthone.

3. A method for reducing malodors of kitchen smells, bathroom smells, smoke and/or sweat, said method comprising applying the detergent composition or personal care composition of claim 1 to a hard surface or human skin having said malodors.

4. The detergent composition or personal care composition of claim 1, wherein the petit grain oil and the peppermint oil are present in a ratio by weight from about 10:1 to about 1:10.

5. The detergent composition or personal care composition of claim 1, wherein the petit grain oil contains linalool and linalyl acetate, the peppermint oil contains menthol and menthone, and the components linalool:linalyl acetate:menthol:menthone present in a ratio by weight of about (1-3):(2.5-5.5):(1-3.5):(0.5-2.5).

6. The detergent composition or personal care composition of claim 1, wherein the hydroxy carboxylic acid ester is triethyl citrate.

7. A detergent composition or personal care composition comprising:
(A) a perfume composition comprising
(a) about 0.1 to about 40 wt % petit grain oil,
(b) about 99.9 to about 60 wt % triethyl citrate,
(c) 1 to about 20 wt % of a terpene and
(d) 1 to about 25 wt % essential oils selected from the group consisting of citronella oil, lavender oil, litsea cubeba oil, palmarosa oil, peppermint oil, pine oil and their mixtures; and
(B) a surfactant in the amount of from 0.1 to 90 wt % based on the total weight of the detergent composition or personal care composition.

8. A method for reducing malodors of kitchen smells, bathroom smells, smoke and/or sweat, said method comprising applying the detergent composition or personal care composition of claim 7 to a hard surface or human skin having said malodors.

9. The detergent composition or personal care composition of claim 1, wherein the perfume composition is present in an amount of from 0.01 to 5% by weight of the detergent composition or personal care composition.

10. The detergent composition or personal care composition of claim 7, wherein the perfume composition is present in an amount of from 0.01 to 5% by weight of the detergent composition or personal care composition.

11. The detergent composition or personal care composition of claim 1, wherein said terpene is in the amount of from 5 to 15 wt % of the perfume composition.

12. The detergent composition of claim 1, wherein the detergent composition is selected from the group consisting of a dish washing detergent, an all-purpose cleaning detergent and a light duty detergent.

13. The personal care composition of claim 1, wherein the personal care composition is selected from the group consisting of a deodorant, a shampoo and a shower gel.

14. The method of claim 3, wherein said terpene in the perfume composition is either limonene or menthone.

15. The method of claim 3, wherein the petit grain oil and the peppermint oil in the perfume composition are present in a ratio by weight from about 10:1 to about 1:10.

16. The method of claim 3, wherein the hydroxy carboxylic acid ester in the perfume composition is triethyl citrate.

17. The method of claim 3, wherein the perfume composition is present in an amount of from 0.01 to 5% by weight of the detergent composition or personal care composition.

18. The method of claim 3, wherein the detergent composition is selected from the group consisting of a dish washing detergent, an all-purpose cleaning detergent and a light duty detergent.

19. The method of claim 3, wherein the personal care composition is selected from the group consisting of a deodorant, a shampoo and a shower gel.

20. The method of claim 8, wherein said terpene in the perfume composition is either limonene or menthone.

21. The method of claim 8, wherein the petit grain oil and the peppermint oil in the perfume composition are present in a ratio by weight from about 10:1 to about 1:10.

22. The method of claim 8, wherein the perfume composition is present in an amount of from 0.01 to 5% by weight of the detergent composition or personal care composition.

23. The method of claim 8, wherein the detergent composition is selected from the group consisting of a dish washing detergent, an all-purpose cleaning detergent and a light duty detergent.

24. The method of claim 8, wherein the personal care composition is selected from the group consisting of a deodorant, a shampoo and a shower gel.

* * * * *